Figure 1:
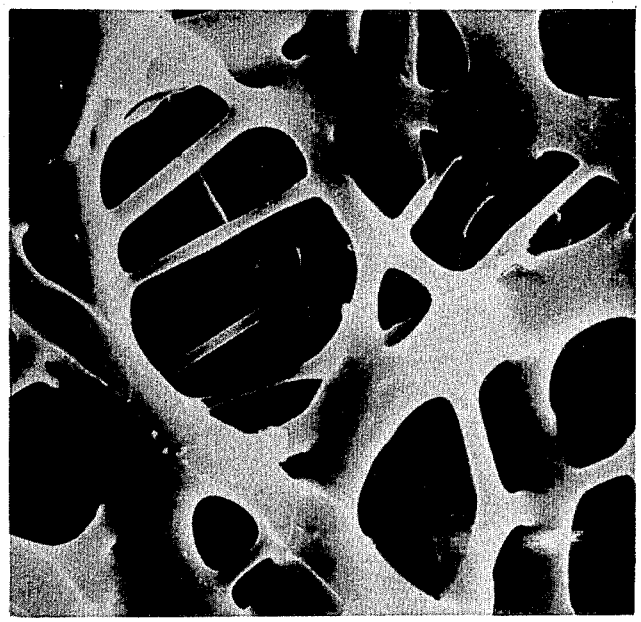

United States Patent [19]

Ehrnford

[11] 4,392,828
[45] Jul. 12, 1983

[54] METHOD FOR RESTORING A TOOTH

[76] Inventor: Lars E. M. Ehrnford, 31 Sanekullavagen, 217 14 Malmo, Sweden

[21] Appl. No.: 226,636

[22] Filed: Jan. 21, 1981

Related U.S. Application Data

[63] Continuation of Ser. No. 777,909, Mar. 15, 1977, abandoned.

[30] Foreign Application Priority Data

Mar. 16, 1976 [SE] Sweden .................................. 7603313

[51] Int. Cl.³ .............................................. A61K 6/08
[52] U.S. Cl. ...................................... 433/217; 106/35; 433/199; 433/201; 433/202; 433/222; 433/228; 523/115; 523/116
[58] Field of Search ............... 433/199, 226, 228, 217, 433/222, 202, 201; 106/35; 523/115, 116

[56] References Cited

U.S. PATENT DOCUMENTS 3,328,230 6/1967 Levecque et al. .................. 161/150
4,055,268 10/1977 Barthel ................................. 220/9 C

FOREIGN PATENT DOCUMENTS 1060716 3/1967 United Kingdom .

OTHER PUBLICATIONS

Bone Tissue Formation Within a Sintered Microporous Glass-Fiber Network Implanted in Extraction Sockets in the Rat, Ehrnford et al., pp. 130-133.

Primary Examiner—Lorenzo B. Hayes
Attorney, Agent, or Firm—Bacon & Thomas

[57] ABSTRACT

A method for restoring a tooth which involves applying to the tooth a glass filler comprising a porous three-dimensional network of inorganic fibres bonded to each other at their points of contact and the porosity of which is substantially continuous throughout the network admixed with a polymeric material.

1 Claim, 2 Drawing Figures

METHOD FOR RESTORING A TOOTH

This is a continuation of application Ser. No. 777,909, filed Mar. 15, 1977, now abandoned.

The present invention relates to a stiffening and reinforcing element and/or retention element, preferably to be used for stiffening and/or reinforcing dental composites and/or retention of implant materials.

It is a desire that dental composites should present properties as similar to the tooth substance as possible with respect to appearance, strength, stiffness and wear resistance. Other important properties of such materials are those which are of special significance for the formation of micro leakage (gap formation between the tooth and filling) such as the thermal expansion coefficient, polymerization contraction and probably also the viscoelastic properties of the materials.

With respect to these factors, a conventional composite material should be such that the organic polymer portion is as small as possible thereby to reduce its significance as a "weak link". There should also be a strong and stable bond between the norganic portion (the filler) and the organic portion (the matrix).

The absence of an adequate bond may, for example, give rise to the effect that particles of filler dislodge from the surface or water is admitted to penetrate along the border surface between the filler and the matrix. This probably represents the main reason for the insufficient resistance to occlusale wear in now existing so-called dental composite restorative resins.

In order to attain a low content of polymer, there is frequently aimed at the inorganic filler particles having a size distribution as broad as possible. The incorporation of big and very abrasion resistant particles may, however, be unfavorable in view of the surface roughness obtained as a result of the uneven wear of the surface.

The object of the present invention is to provide a stiffening and reinforcing element and/or retention element which fulfills high reqirements for appearance, strength, stiffness and wear resistance or fulfills high requirements for living tissue attachment. According to the invention, this object is mainly attained by the feature that the stiffening and reinforcing element and/or retention element consists of porous inorganic material having a three-dimensional net-work structure consisting of individual fibres of the inorganic material, said fibres being firmly bonded to each other.

Figure 2:
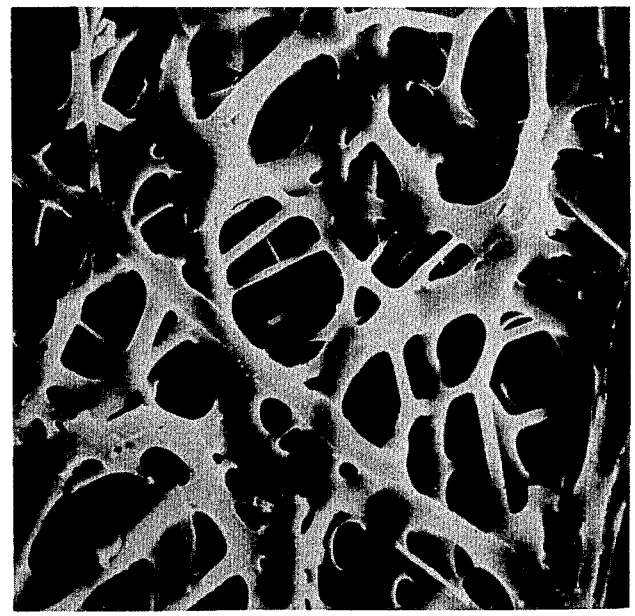

A partial enlargement of the element according to the invention is illustrated in FIGS. 1 and 2 comprising photographs of the element.

The element according to the invention consists of a porous inorganic material having a three-dimensional net-work structure consisting of fibres of the inorganic material, said fibres being firmly bonded to each other.

The porous inorganic material may suitably be polymer impregnated and the pores between the fibres may form a continuous system to make it possible to carry out a deep impregnation. The impregnation results in an increased strength and stiffness and increased wear resistance of the material. Suitable impregnating agents are hardening (thermosetting or thermoplastic resins such as methyl methacrylate, epoxy resins or a combination of methyl methacrylate and epoxy resins from the reaction product of Bisphenol and glycidly acrylate, which resins are well known in the prior art as "Bowen-resins" and disclosed by the Bowen U.S. Pat. No. 3,066,112.

The stiffening and reinforcing effect and the attachment capability of the element according to the invention is particularly advantageous when the fibres are made from glass. In order that the element may obtain a favorable surface structure after wear the diameter of the fibres should be less than $100\mu$, preferably less than $10\mu$, after sintering.

Satisfactory attachment an implantation and the living tissue requires either good adhesion or a mechanical locking which may be achieved, e.g. by permitting the tissue to grow into superficial pores. An element according to the invention combines these two properties in that it may be attached by tissue ingrowth on the one hand and that the tissue adheres to glass in a particularly excellent manner on the other hand.

In order that the fibres of the porous inorganic material may be bonded firmly to each other thereby to establish the three-dimensional net-work structure the fibres must be fused together, and this perferably takes place by heating the fibres by means of a suitable heat source or by vibrating the fibres thereby to heat them and cause them to fuse together at the contact points.

An example of materials and methods used for the manufacture of the element according to the present invention will now be described.

EXAMPLE

For the manufacture, there is used a down of A-glass type fibres (Gullfiber AB, Billesholm, Sweden) having an extremely small fiber diameter ($<4\mu$). A combined heating and pressure treatment yielded combinations that resulted in the fibres being fused together to a tight net-work. The latter was then impregnated with "Bowen-resin" by means of a vacuum method similar to that previously described for the manufacture of a gypsum polymer composite (Ehrnford, 1972, Swedish public specification No. 362 060).

For scanning electron microscopic studies, $250\mu$ thick sheets were made by compressing downs of fibres under a pressure of 4000 Pa between plates of mica at about 650° C.

In vacuum and during rotation the test pieces were coated with an about 200 Å thick layer of a vaporized alloy of palladium and gold (40% of palladium and 60% of gold).

The morphology in the layers of the sheets adjacent to the mica plates were studied in an electron microscope (Cambridge Stereoscan Mark II) and photographic registration thereof was made on an Ilford Pan F film.

While the polymer in a fiber net-work prepared according to the above example may bond chemically to the matrix polymer, a mechanical interlocking of the reinforcing element is obtained.

A net-work prepared according to the above example may be used as a retention element prior to impregnation, for example, in the form of a surface coating on an implantation.

The pictures reveal that the fibres are fused together to a glass skeleton which is crossed by a micropore system. This glass skeleton may be used as a retention element and presents a structure favorable from strength, stiffness and adhesion viewpoints. The surfaces thereof are smooth and have no detectable defects capable of indicating fractures.

Thus, the pictures clearly disclose that the fibres have been combined into a three-dimensional net-work. The interstices form a continuous system which renders the material capable of undergoing deep impregnation. Such a deep impregnation may be suitable to carry out with longer units of the material, said units being converted into e.g. a particulate filler material after curing of the impregnating agent. In this connection, the impregnating agent of the filler need not to be identical with the matrix substance.

Due to the possibility of imparting a varying composition also to the inorganic component several possibilities of influencing the properties of the filler will arise.

Besides as a particulate filler, the inorganic net-work may be used in large profile elements for filling, stiffening and reinforcing of dental restoration and construction materials and can as well be used as an implant material.

It is obvious for a person skilled in the art that the element according to the invention may be subjected to modifications and changes with respect to its composition and field of application without departing from the scope of the invention as defined in the attached claims.

I claim:

1. A method of restoring a tooth which comprises applying thereto a dental composite comprising a particulate glass filler comprising a rigid and porous three-dimensional network of glass fibers produced by fusing together by heating the fibers having a diameter of less than 4 microns at a temperature sufficient to cause melting and complete fusion of substantially all of the individual glass fibers at their points of contact, the porosity of which is substantially continuous throughout the network, and mixed in an organic hardening resin; and allowing sufficient time for the hardening thereof.

* * * * *